United States Patent
Glide-Hurst et al.

(10) Patent No.: US 12,396,700 B2
(45) Date of Patent: Aug. 26, 2025

(54) FLEXIBLE MODULAR PHANTOM AND METHOD FOR MEDICAL APPLICATIONS USING INTERCHANGEABLE INSERTS

(71) Applicant: Wisconsin Alumni Research Foundation, Madison, WI (US)

(72) Inventors: Carri Glide-Hurst, Middleton, WI (US); Kenneth Gregg, Cleveland, OH (US)

(73) Assignee: Wisconsin Alumni Research Foundation, Madison, WI (US)

( * ) Notice: Subject to any disclaimer, the term of this patent is extended or adjusted under 35 U.S.C. 154(b) by 222 days.

(21) Appl. No.: 18/226,390

(22) Filed: Jul. 26, 2023

(65) Prior Publication Data

US 2025/0032083 A1  Jan. 30, 2025

(51) Int. Cl.
    *A61B 6/58*  (2024.01)
(52) U.S. Cl.
    CPC .................................. *A61B 6/583* (2013.01)
(58) Field of Classification Search
    CPC .................. A61N 5/10; A61N 5/1075; A61N 2005/1076; A61N 5/1048; A61N 5/1037; A61N 2005/1072; G01T 1/169; B33Y 80/00; G09B 23/32; G09B 23/288; A61B 6/583; A61B 6/037
    See application file for complete search history.

(56) References Cited

U.S. PATENT DOCUMENTS

| | | | |
|---|---|---|---|
| 9,797,975 B2 | 10/2017 | Yin et al. | |
| 9,857,443 B2 | 1/2018 | Tadic et al. | |
| 10,463,885 B2 | 11/2019 | Scheib | |
| 11,510,658 B2 | 11/2022 | Speidel et al. | |
| 12,097,385 B2 * | 9/2024 | Kang | G09B 23/30 |
| 2008/0298540 A1 * | 12/2008 | Serban | A61N 5/1048 378/18 |
| 2017/0042502 A1 * | 2/2017 | Koo | A61B 6/032 |
| 2020/0146647 A1 | 5/2020 | Uber, III et al. | |
| 2020/0232938 A1 | 7/2020 | Fitzgerald et al. | |

FOREIGN PATENT DOCUMENTS

| | | |
|---|---|---|
| WO | 2016137425 | 9/2016 |
| WO | 2017019809 | 2/2017 |

OTHER PUBLICATIONS https://www.ptwdosimetry.com/en/products/ruby-modular-qa-phantoms, Jun. 15, 2023.
Gillian QA Phantom (p. 10)—Imaging Solutions, QA Phantoms, 2015, Version 0615.

* cited by examiner

*Primary Examiner* — David P Porta
*Assistant Examiner* — Fani Polyzos Boosalis
(74) *Attorney, Agent, or Firm* — Boyle Fredrickson, S.C.

(57) ABSTRACT

The present invention provides a phantom assembly for placement of implant structures (e.g., solid tumor and normal organ surrogates) and/or optional imaging fluids (e.g., liquid or gel) for diagnosis and treatment planning. The present invention provides a capsule receiving cavity inserts allowing for the placement of implant structures, radiation detectors/measurement devices, imaging fluids, and the like within the capsule for image quality evaluation, target localization, treatment planning, and dosimetry measurements. The present invention may incorporate motion components to enable motion-resolved experimentation in imaging and radiation therapies.

20 Claims, 5 Drawing Sheets

FLEXIBLE MODULAR PHANTOM AND METHOD FOR MEDICAL APPLICATIONS USING INTERCHANGEABLE INSERTS

STATEMENT REGARDING FEDERALLY SPONSORED RESEARCH OR DEVELOPMENT

This invention was made with government support under HL 153720 awarded by the National Institutes of Health. The government has certain rights in the invention.

CROSS REFERENCE TO RELATED APPLICATION

N/A

Background of the Invention

The present invention relates to a medical phantom for surgical planning, clinical training, medical imaging, radiotherapy applications, and the like, and in particular, a medical phantom assembly that is able to support various bulk model structures and treatment protocols for multiple imaging modalities.

A medical phantom is a medical device that mimics the human body or a part of the human body such as human tissue and organs. Phantoms are usually made of hard, soft, and digital materials that mimic the responses of human tissues under certain conditions. For example, materials are selected based on density, stretchability, hardness, and the like. Phantoms are used in medical imaging and radiotherapy for multiple applications including radiotherapy and surgical planning, imaging validation, equipment calibration, quality assurance and validation, and education.

Radiation therapy, also called radiotherapy, involves precise targeting of x-rays beams or other particles to destroy cancers cells or other non-malignant conditions. For example, radiation therapy may be used to deliver ablative radiation doses to arrhythmogenic scar regions of the heart to stop abnormal heart rhythms (ventricular tachycardia) as a noninvasive treatment of refractory ventricular tachycardia according to some promising initial data. In radiotherapy, phantoms are used for routine quality assurance, dosimetry, and end-to-end testing.

Challenges that are often encountered during radiotherapy include tumor motion, tissue motion and/or deformation, and other heterogeneities in the radiation beam path which affect the delivery of radiation doses to the tumor or target and can adversely affect the surrounding healthy tissues or organs, or organs at risk (OAR), positioned near the cancer cells. For example, respiratory motion, if not taken into consideration, can affect the delivery of radiation doses to the tumor or tumor site, e.g., thoracic tumors, or to other targets, e.g., ventricular scars from infarction or replacement fibrosis or arrhythmogenic regions of the heart for ventricular tachycardia. Therefore, phantoms can assist with the planning of a specific treatment plan, e.g., plan appropriate radiation doses, that considers tissue and tumor motion and/or deformation.

Therefore, there is a need to better account for moving structures or fluids that are critical for diagnosis of disease and the precise localization needed for treatment planning, e.g., surgical and radiation planning.

One of the challenges of designing phantoms is that phantoms are typically customized to fit specific imaging systems. For oncology applications, single photon emission computed tomography (SPECT), positron emission tomography (PET), computed tomography (CT), and magnetic resonance imaging (MRI) are typical imaging modalities. Specific phantoms are used to satisfy the needs of each imaging method.

For example, CT imaging employs x-rays to measure the attenuation properties of biological tissue. Therefore, materials with different attenuation coefficients are used to generate CT phantoms with good contrast. Many CT phantoms are based on simple heterogenous structures using solid materials that mimic the x-ray attenuation properties of human tissues.

In contrast, MRI measures electromagnetic radiation originating from the realignment of excited nuclear magnetic moments. The magnetic moments of hydrogen atoms are targeted in biological tissue resulting in different signal intensities. Solid materials produce relaxation times that are too short for MRI to detect and therefore require tissue-mimicking materials, such as water, fat, and agarose gel. Many MRI phantoms rely upon embedding solid materials into water, fat or agarose gel.

Therefore, there is further need for phantoms that can be adapted for use with several imaging modalities without compromising the ability to simulate body motion and provide motion management.

SUMMARY OF THE INVENTION

The present invention provides a modular phantom assembly that can be adapted for use with several imaging modalities and simulated scenarios involving body motion.

The present invention further provides a phantom assembly for placement of implant structures (e.g., solid tumor, other targets, and normal organ surrogates) and/or imaging fluids (e.g., liquid or gel) for image quality evaluation, target localization, treatment planning, and dosimetry measurements.

The present invention further provides a phantom assembly that uses implanted anthropomorphic (e.g., human-like) geometry that can flexibly demonstrate different human conditions to facilitate high precision radiation therapy and mimic clinical use cases across different disciplines.

The present invention further provides an outer capsule receiving cavity inserts allowing for the placement of implant structures, radiation detectors/measurement devices, imaging fluids, and the like within the capsule for image quality optimization and target localization. The present invention may incorporate motion components to enable motion-resolved experimentation in imaging and radiation therapies.

The present invention further provides a phantom assembly that permits precise targeting and dose delivery to singular or multiple "active" points in simple or complex (e.g., anthropomorphic) geometries with one or more targets.

In one embodiment, the present invention provides a phantom assembly for medical imaging comprising a watertight chamber having an outer wall supporting a volume therein and enclosed by first and second end plates; and at least one tube connector of the first and second end plates configured to removably receive at least one tube supported by the first and second end plates, each tube providing a volume therein.

It is thus a feature of at least one embodiment of the present invention to permit interchangeable and removable tubing to be suspended within the chamber for flexible use including supporting phantom inserts.

At least one tube may be received by the at least one tube connector.

It is thus a feature of at least one embodiment of the present invention to allow the chamber to removably support the tubing in a manner in which tubes can be added or removed.

The at least one tube connector may comprise a channel receiving an end of the at least one tube.

It is thus a feature of at least one embodiment of the present invention to permit an inner lumen of the tube to be accessible through the end plate of the chamber to hold various items within the tube at controlled positions.

At least one channel stopper may be insertable into the at least one channel when a tube is not inserted into the channel.

It is thus a feature of at least one embodiment of the present invention to water seal the chamber when tubes are removed or less tubes are needed providing flexibility of use.

Screw adapters may removably receive the at least one tube or the at least one channel stopper on an exterior of the watertight chamber.

It is thus a feature of at least one embodiment of the present invention to seal the channels to maintain a watertight seal of the chamber.

The at least one channel stopper may comprise of screw heads and threaded screw ends permitting the at least one channel stopper to be screw tightened into the at least one channel.

It is thus a feature of at least one embodiment of the present invention to use threaded screw connections for easily interchanging the channels with channel stoppers or tubes.

A gasket may be positioned between the first and second end plates and the at least one channel stopper.

It is thus a feature of at least one embodiment of the present invention to seal the connection of the screw adapters and the channel stoppers to prevent leakage at the channels.

The at least one tube may comprise threaded screw ends permitting the at least one tube to be screw tightened into the at least one channel.

It is thus a feature of at least one embodiment of the present invention to permit access to the inner lumen of the tubes using an outer screw threading on the tubes.

A gasket may be positioned between the first and second end plates and the threaded screw ends of the at least one tube.

It is thus a feature of at least one embodiment of the present invention to connect the tubes to the end plates using a simple finger tightening mechanism while still permitting the tubes to support items therein at desired positions A motor assembly may be connectable to the chamber and may actuate movement of the chamber. A motor or pump assembly may also assist with conducting fluid flow through the chamber.

It is thus a feature of at least one embodiment of the present invention to permit motion of the chamber to simulate human motion for more precise radiation planning.

The motor assembly may be configured to move the chamber in a linear direction and non-linear direction.

It is thus a feature of at least one embodiment of the present invention to permit motion management to be implemented by the same device compatible with different imaging modalities.

A solid phantom may be supported by the at least one tube and mimicking at least part of a human body part.

It is thus a feature of at least one embodiment of the present invention to permit suspension of a solid phantom within a fluid of the chamber thus permitting certain modalities, such as MRI. It is also a feature of at least one embodiment of the present invention to permit the tubes to carry body-like structures for medical imaging and treatment such as tumor surrogates, fluid-filled vessels with directional flow emulating arteries or veins, etc.

A radiation measurement device may be supported by the at least one tube. The radiation measurement device may also be suspended in the fluid chamber, e.g., polymer gel dosimeters.

It is thus a feature of at least one embodiment of the present invention to allow for dosimeter measurements with solid phantoms by extending the dosimeters through the solid phantom.

One or more radiation measurement devices may be extended through the at least one tube and further comprise a connector connecting the radiation measurement device to an exterior of the at least one tube. Other devices that may be extended through the at least one tube include pacemaker leads, stents, wire meshes, etc. for clinical evaluation such as through image quality evaluation.

It is thus a feature of at least one embodiment of the present invention to permit the tubes (with or without liquid or similar) to carry cable connectors (e.g., electrical, fiber-optic, etc.) for transfer of information to read out to active dosimeter devices. It is also a feature of at least one embodiment of the present invention to permit the tubes to carry radioactive substances for imaging modalities that require emission of radiation (e.g., PET) from the phantom body.

A distance measuring device such as a caliper, ruler, or multiple known spacers, or other means, may be used to precisely control the position of an object within a tube from either direction.

The watertight chamber may be, optionally, fillable with a fluid. The fluid may be a liquid or gel.

It is thus a feature of at least one embodiment of the present invention to allow for imaging which requires mimicking of tissue deformation such as MRI.

One embodiment of the present invention provides a method of imaging a phantom assembly for treatment planning comprising: providing a watertight chamber having an outer wall supporting a volume therein and enclosed by first and second end plates and at least one tube removably supported by the first and second end plates, each tube providing a volume therein wherein the first and second end plates each provide a plurality of channels of the first and second end plates and removably receiving the at least one tube; connecting at least one tube to the plurality of channels; connecting at least one stopper to channels where a tube is not connected; inserting a solid phantom mimicking at least part of a human body part into the watertight chamber and supported by the at least one tube; sealing the watertight chamber; and imaging the watertight chamber using a medical imaging technique.

The method may include inserting a radiation measurement device into the at least one tube prior to imaging and measuring a radiation dose.

The method may include filling the watertight chamber with a liquid prior to imaging.

The medical imaging technique may be any one of single photon emission computed tomography (SPECT), positron emission tomography (PET), computed tomography (CT), and magnetic resonance imaging (MRI).

These particular objects and advantages may apply to only some embodiments falling within the claims and thus do not define the scope of the invention.

DETAILED DESCRIPTION OF THE PREFERRED EMBODIMENT

Figure 1:
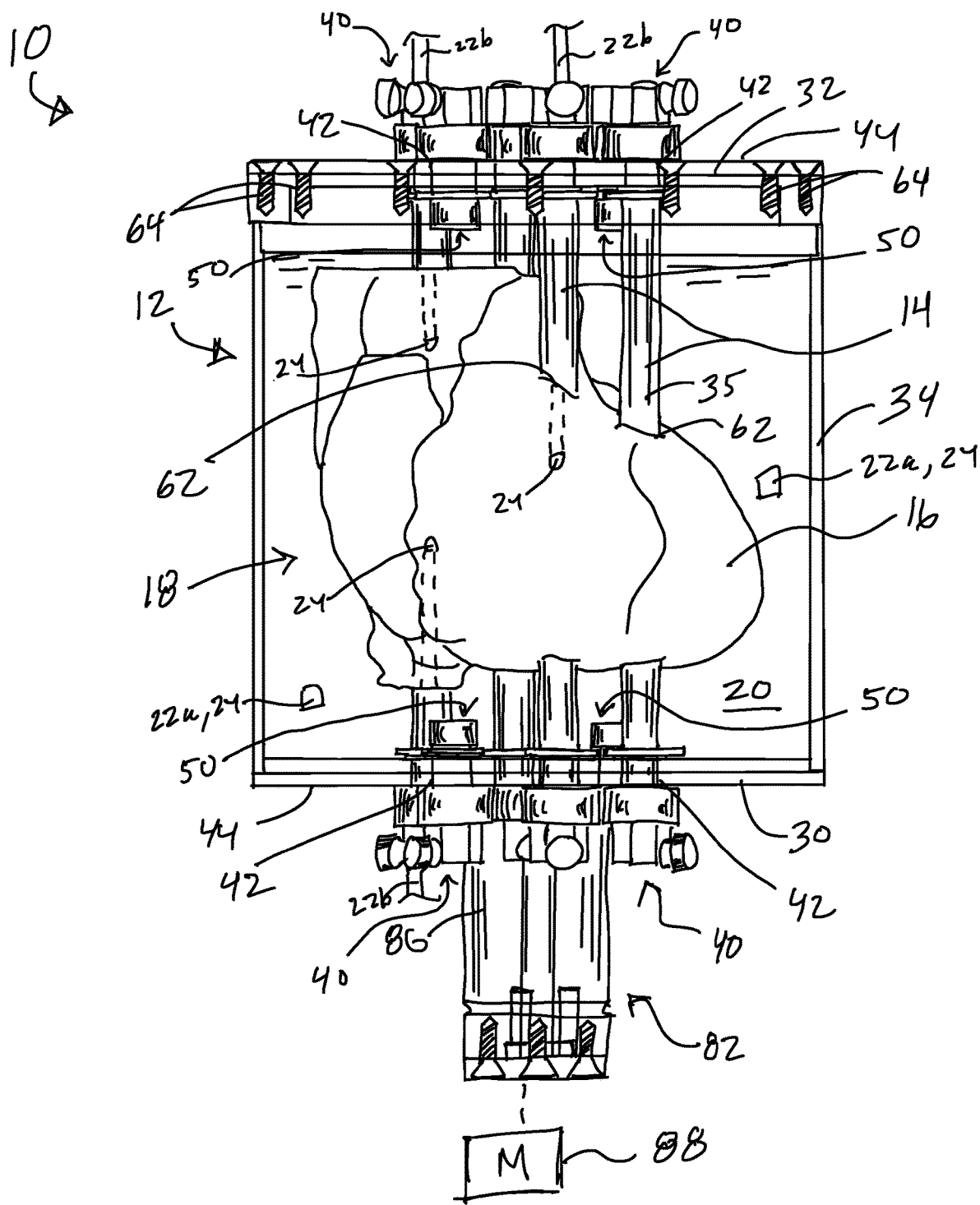
FIG. 1 is a side elevation view of a phantom assembly of one embodiment of the present invention having an outer capsule supporting removable hollow rods extending therethrough and able to support a phantom insert, e.g., resembling a human heart, the outer capsule attachable to a motor assembly to mimic body movements compatible with multiple imaging modalities.

Referring initially to FIG. 1, a phantom assembly 10, constructed according to one embodiment of the present invention, may provide a phantom capsule 12 supporting removable hollow rods 14 extending through the phantom capsule 12 and enabling the suspension of phantom inserts 16, e.g., solid anthropomorphic structures, within a fillable volume 18 of the phantom capsule 12. The fillable volume 18 may be filled with a fluid 20, e.g., a gel or liquid such as deionized water or water-based gel, to assist with imaging. The hollow rods 14 are removable and interchangeable to allow for flexibility in use and may support radiation detectors and measurement devices 22 as further described below.

Figure 2:
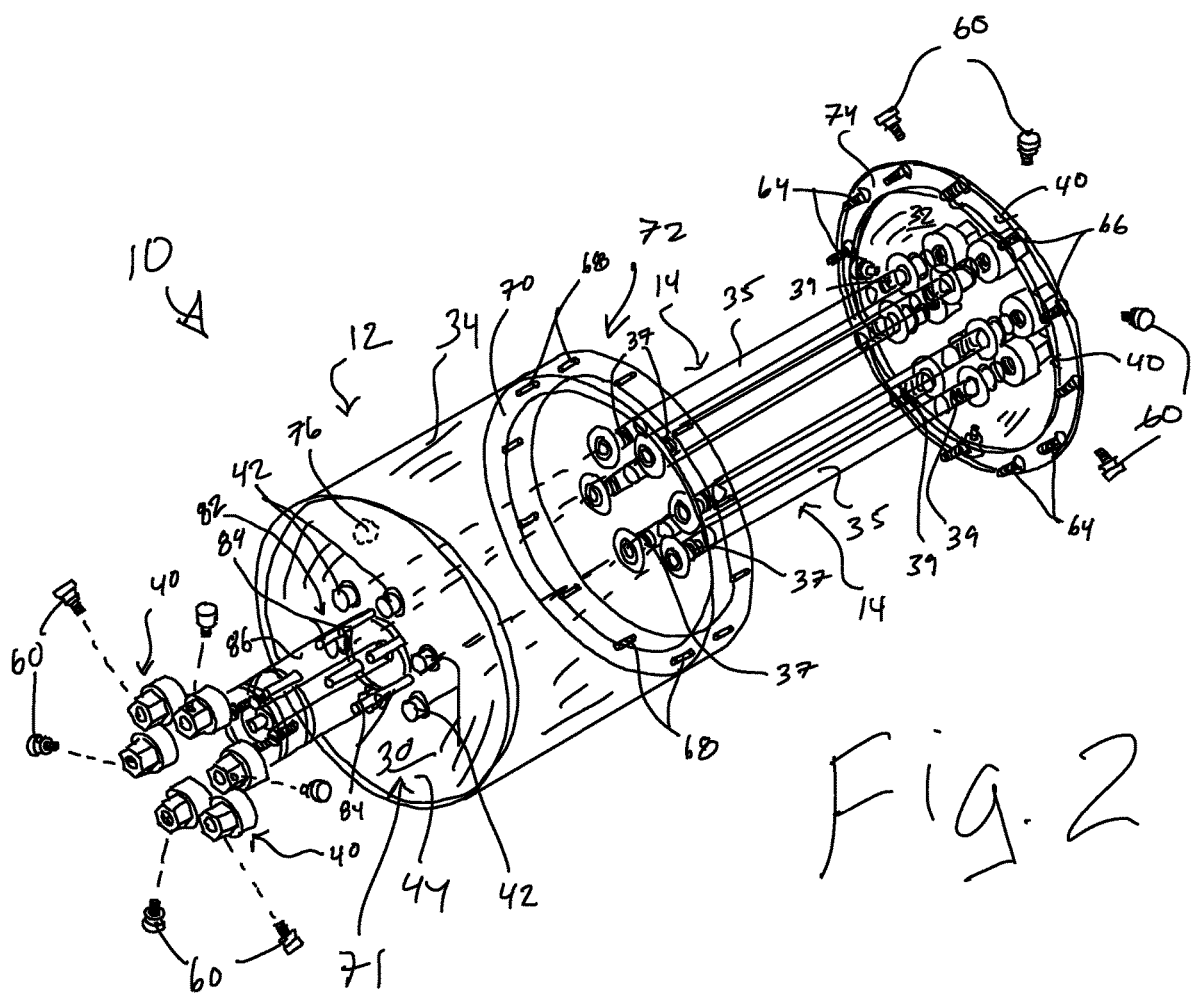
FIG. 2 is an exploded view of the phantom assembly of FIG. 1 showing the outer capsule supporting the removable hollow rods extending therethrough and having a first end plate permitting attachment to the motor assembly and a removable second end plate coupling with a cylindrical sidewall.

Referring also to FIG. 2, the phantom capsule 12 may be defined by a cylindrical housing having a curved, cylindrical sidewall 34 enclosed by opposed first and second end plates 30, 32. The phantom capsule 12 may have a diameter of about 6 inches and may be at least 6 inches and at least 7 inches and at least 8 inches and at least 9 inches and at least 10 inches, and may have a length of about 6 inches and at least 7 inches and at least 8 inches and at least 9 inches and at least 10 inches, desirably sized to receive and support various sized phantom structures therein. The phantom capsule 12 may be made of a clear plastic material such as acrylic, polystyrene, polymethyl methacrylate (PMMA), and the like. In certain embodiments, the phantom capsule 12 may be deformable.

It is understood that the phantom capsule 12 make take various geometric shapes and sizes, e.g., square, rectangular, triangular, round, irregular and the like, or may be realistic to reflect anatomical features.

The phantom capsule 12 may support a plurality of removable hollow rods 14 which extend through the phantom capsule 12. The removable hollow rods 14 may be tubes with a body portion 35 separating a first attachment end 37 opposite a second attachment end 39. The outer surface of the opposed first and second attachment ends 37, 39 of the removable hollow rods 14 are threaded to provide a screw thread attachment of the hollow rods 14 to outer screw adapters 40 providing a tight coupling of the hollow rods 14 to the first and second end plates 30, 32, respectively, as further described below. The hollow rods 14 may have a length of about 6 inches and at least 7 inches and at least 8 inches and at least 9 inches and at least 10 inches. The hollow rods 14 may be at least as long as the length of the phantom capsule 12 to extend outwardly exterior to the phantom capsule 12, for example, extending at least one inch on the exterior sides of the phantom capsule 12. The hollow rods 14 may have an inner lumen with a diameter of about 0.2 inches and about 0.3 inches and about 0.4 inches and about 0.5 inches and an outer diameter of about 0.2 inches and about 0.3 inches and about 0.4 inches and about 0.5 inches. The hollow rods 14 may be made of a clear plastic material such as acrylic, polystyrene, polymethyl methacrylate (PMMA), and the like. The hollow rods 14 may be rigid or flexible, for example, elastic or rubber tubes. While described as straight rods above, the hollow rods 14 may be curved or bending along a non-straight path within the fillable volume 18.

In alternative embodiments, one end of the removable hollow rod 14 is a closed end 46 to allow the removable hollow rod 14 to terminate within the fillable volume 18 instead of extending to the opposite end of the phantom capsule 12. In this respect, the length of the removable hollow rods 14 is less than a length of the phantom capsule 12. The outer screw adapters 40 may assist with supporting the hollow rod 14 at one or both ends of the phantom capsule 12 to extend into or through the fillable volume 18 as desired.

The first end plate 30 and second end plate 32 enclosing the opposed ends of the phantom capsule 12 may be circular plates, each holding a plurality of cylindrical channels 42, e.g., one channel, two channels, three channels, four channels, five channels, six channels, several channels, eight channels, nine channels, ten or more channels, permitting the insertion of the first and second attachment ends 37, 39 of the removable hollow rods 14 therethrough. The plurality of channels 42 may be arranged in a circular configuration or concentric circle configuration that are aligned across the first end plate 30 and second end plate 32 so that the removable hollow rods 14 extend straight across in a circular pattern within the phantom capsule 12. In certain embodiments, the plurality of channels 42 may not need to be aligned so that the removable hollow rods 14 extend at an angle or diagonal across the phantom capsule 12 instead of straight across the phantom capsule 12.

It is understood that any number of channels 42 may be included in the first end plate 30 and second end plate 32, and the channels 42 may be arranged in any desired pattern or configuration. In a preferred embodiment, the center of at least one of the first end plate 30 and second end plate 32 may be clear of any channels 42 to allow for the connection of a motor drive assembly 82 as further discussed below.

Figure 3:
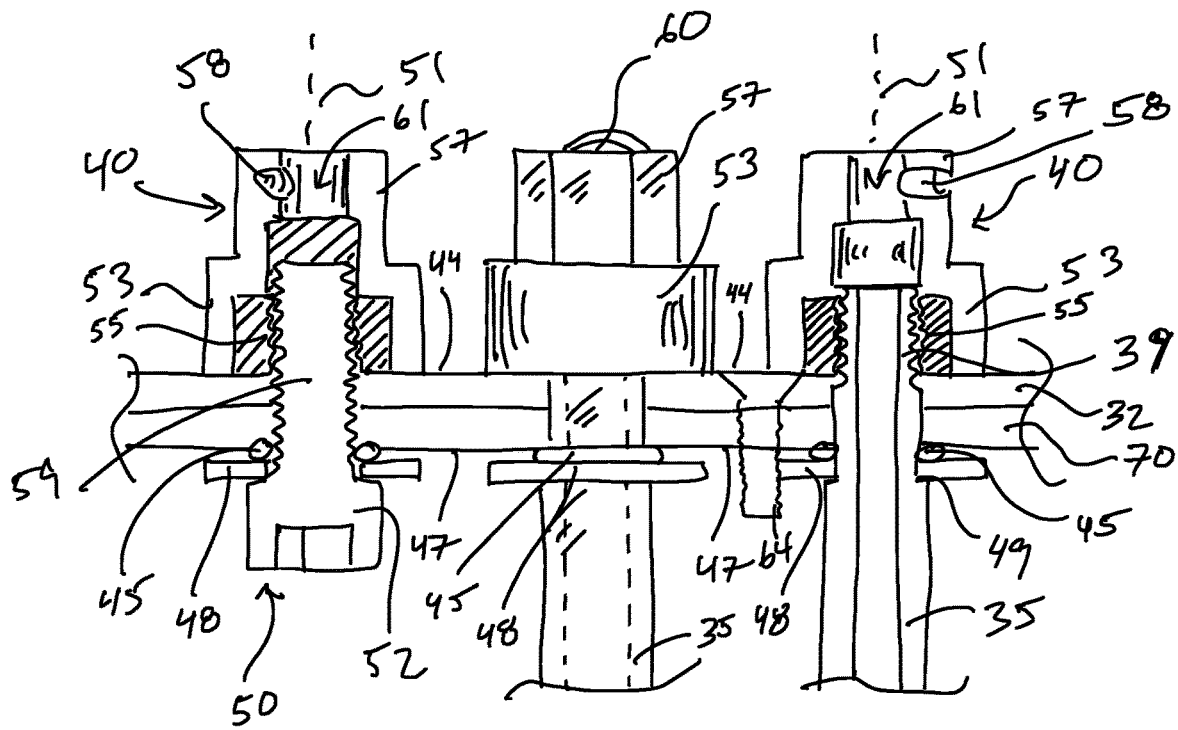
FIG. 3 is an enlarged partial cross section of channels of the removable second end plate of FIGS. 1 and 2 connected to the cylindrical sidewall and supporting attachment of the removable hollow rods or alternatively stoppers if the removable hollow rods are not attached.
Figure 4:
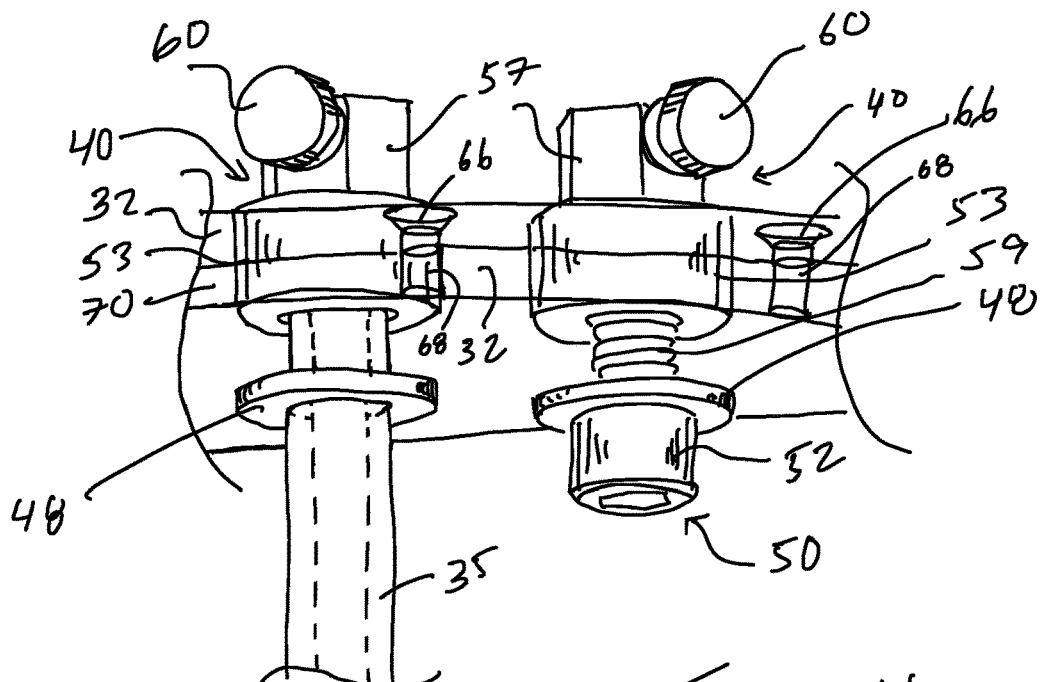
FIG. 4 is an enlarged perspective view similar to FIG. 3 of the channels of the removable second end plate receiving the removable hollow rods or alternatively stoppers if the removable hollow rods are not needed.

Referring to FIGS. 3 and 4, the first and second attachment ends 37, 39 of the removable hollow rods 14 extend outwardly through the channels 42 of the first end plate 30 and second end plate 32, respectively, so that the first and second attachment ends 37, 39 are positioned on an outer surface 44 of the first end plate 30 and second end plate 32 and on the outside of the phantom capsule 12 (although the second end plate 32 is shown, the attachment of the removable hollow rods 14 to the first end plate 30 would be similar).

A watertight connection of the outer wall of the removable hollow rods 14 to the first end plate 30 and second end plate 32 is created on the inside of the phantom capsule 12 capsule and is assisted by a mechanical gasket such as an inner O-ring 45 pressed against an inner surface 47 of the first and second end plate 30, 32 and an outer washer 48 held within a groove 49 of the body portion 35 of the removable hollow rod 14 and pressed against the O-ring 45 and the body portion 35 of the removable hollow rod 14. The inner surface 47 at the edge of the channel 42 may include functionality to assist with the placement of the O-ring 45 and provide an inward force against the hollow rod 14 to assist with sealing. The inner O-ring 45 and outer washer 48 together provide a watertight or airtight seal of the outer wall of the removable hollow rods 14 against the inner surface 47 of the first and second end plate 30, 32.

On the exterior of the phantom capsule 12, the first and second attachment ends 37, 39 of the removable hollow rods 14 are further screwed into the outer screw adapters 40 along a screw direction 51 on the outer surface 44 of the first and second end plate 30, 32, respectively. The outer screw adapters 40 provide a cylindrical base 53 having a female thread fitting 55 on its interior and a hexagonal cap 57 extending outwardly from the cylindrical base 53 and supporting a circular hole 61 therein. The cylindrical base 53 and the hexagonal cap 57 are hollow along the screw direction 51 thus providing a path for radiation detectors and measurement devices 22 to be inserted into the removeable hollow rods 14 through the top opening of the circular hole 61 of the hexagonal cap 57.

The cylindrical base 53 includes a perpendicular hole 58 receiving a fastener 60 such as one or more set screws or thumb screws extending perpendicular to the screw direction 51 of the female thread fitting 55, for example, to attach the outer screw adapters 40 to a mounting assembly.

The outer screw adapter 40 is held tightly against the outer surface 44 of the first and second end plate 30, 32 by screwing the first and second attachment ends 37, 39 into the female thread fitting 55 thus tightening the screw connection between the outer screw adapter 40 and the first and second attachment ends 37, 39 and pressing the O-ring 45 and outer washer 48 against the inner surface 47 of the first and second end plate 30, 32. The female thread fitting 55 within the cylindrical base 53 may include a thread sealant to prevent leakage of fluids within the threaded connection.

When a removable hollow rod 14 is not inserted into one or more of the channels 42, the channel 42 may be filled with a removable stopper 50 which may comprise of a screw body 59 with a screw head 52 held against the inner surface 47 of the first end plate 30 and supporting therebetween a mechanical gasket such as an inner O-ring 45 pressed against the inner surface 47 of the first end plate 30 and an outer washer 48 pressed between the O-ring 45 and the screw head 52.

The screw body 59 includes a threaded outer surface that, on an exterior of the phantom capsule 12, is screwed into the outer screw adapter 40, as described above, on an outer surface 44 of the first and second end plate 30, 32 whereby the screw body 59 is rotated to tighten the screw connection between the outer screw adapter 40 and the removable stopper 50 and to press the O-ring 54 and the outer washer 56 against the inner surface 47 of the first and second end plate 30, 32. Similar to the connection of the removable hollow rod 14 to the first and second end plate 30, 32, the inner O-ring 54 and the outer washer 56 provide a watertight or airtight seal of the stopper 50 against the inner surface 47 of the first and second end plate 30, 32.

Thus, it is understood that the removable hollow rod 14 and the stoppers 50 may be interchanged in any combination while still water sealing the phantom capsule 12.

Figure 5:
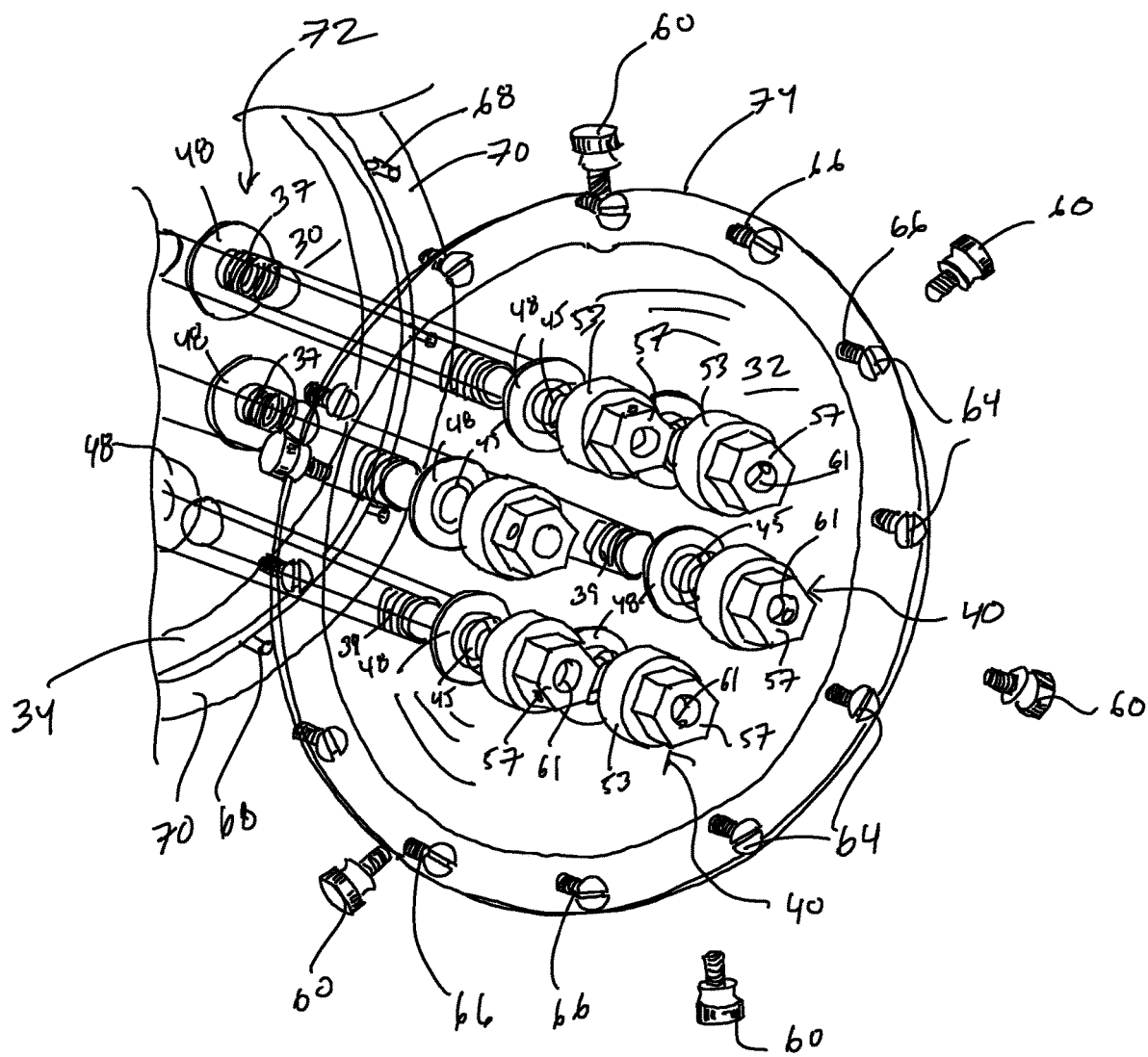
FIG. 5 is an end perspective view of the exploded phantom assembly of FIG. 2 showing the removable second end plate detached but attachable to the cylindrical sidewall by screws and the removable hollow rods detached but attachable to the second end plate by screw adapters.

Referring now to FIG. 2 and FIG. 5, the first end plate 30 may be integrally formed with the cylindrical side wall 34 to provide a closed end 71 opposite an open end 72.

The second end plate 32 may be attached to the cylindrical side wall 34 by a plurality of fasteners 64 extending through holes 66 around a perimeter of the second end plate 32 and screwed into a plurality of screw holes 68 on an inwardly extending rim 70 on the open end 72 of the cylindrical side wall 34 receiving the second end plate 32. A gasket 74 may be positioned between the second end plate 32 and the inwardly extending rim 70, to provide a watertight or airtight seal between the second end plate 32 and the cylindrical side wall 34 at the open end 72.

It is understood that either or both of the first end plate 30 and second end plate 32 may be joined to the cylindrical side wall 34 by fasteners 64 as described with respect to the second end plate 32 above. It is also understood that the first end plate 30 and/or second end plate 32 may be sealingly joined to the cylindrical side wall 34 using alternative attachment methods known in the art such as an outer screw thread attachment, friction fit connection, and the like.

Referring to FIGS. 1 and 2, in one embodiment, the first end plate 30 may support a mounting stem 80 permitting the attachment of the motor drive assembly 82. In this respect, a center of the first end plate 30 may by clear of any channels 42 and instead include a mounting stem 80 that includes a plurality of outwardly extending connection rods 84 attachable to a shaft 86 further coupled to a motor 88 such as a piezo motor or stepper motor which provides non-linear (e.g., rotational, sinusoidal or oscillating) and/or linear motion to the phantom capsule 12 of the phantom assembly 10 to mimic body motion. In this respect, the entire phantom capsule 12 is actuated to mimic motion of the body, e.g., the respiratory motion of the diaphragm or cardiac motion. The motor drive assembly 82 may be compatible with MRI, and therefore, may be made of nonmagnetic and dielectric materials, such as plastics, ceramics, and rubbers, or shielded, so as to not adversely affect the imaging.

In certain embodiments, the motor drive assembly 82 may assist with applying a controlled compression onto the phantom assembly 10, for example, on phantom inserts 16 which are deformable or to assist with fluid flow through the fillable volume 18.

Figure 6:
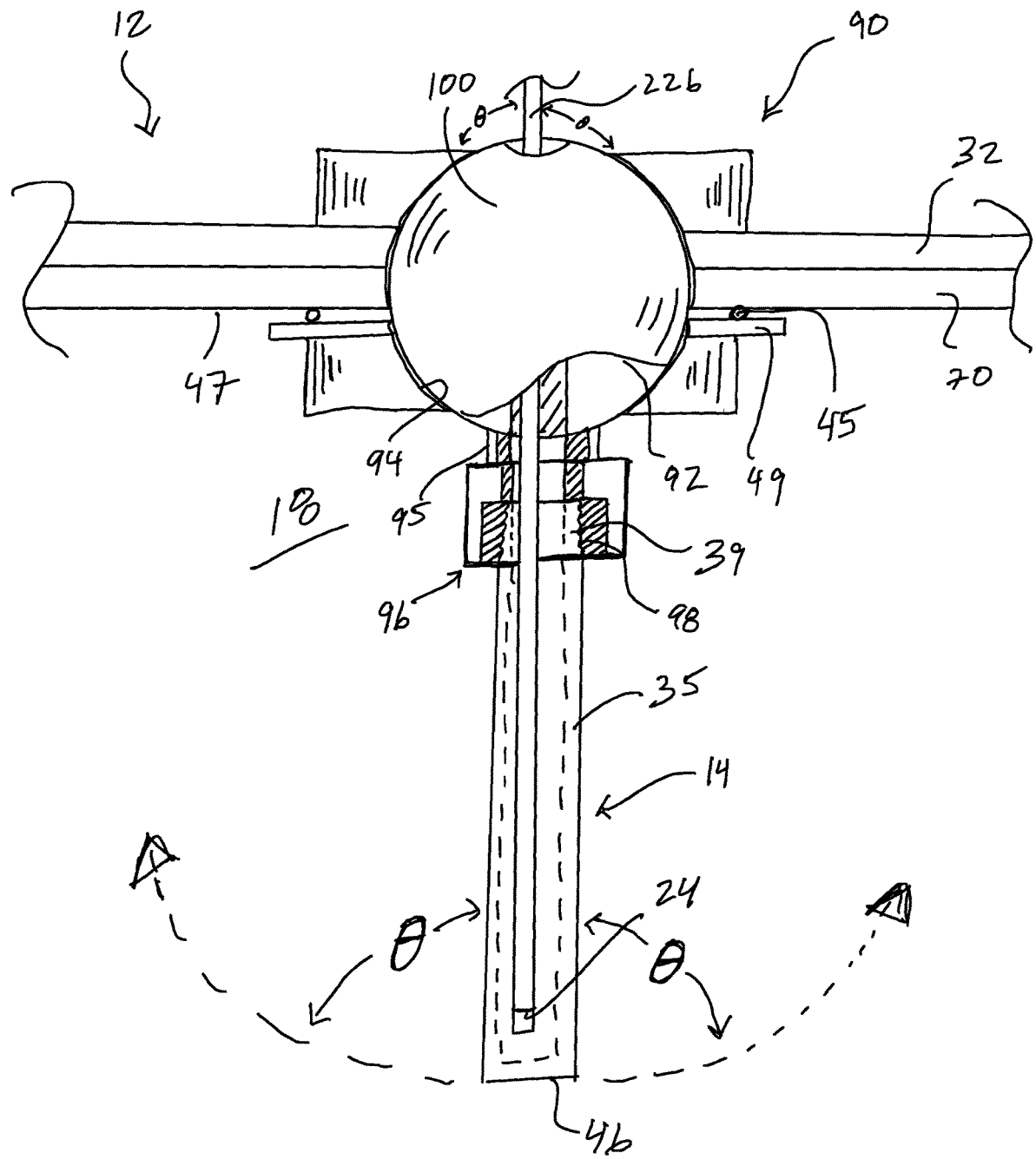
FIG. 6 is a partial cross section of an alternative embodiment of the present invention showing the removable second end plate supporting attachment of a ball joint allowing removable hollow rods to be angled and terminate within the outer capsule.

Referring briefly to FIG. 6, in an alternative embodiment, the channels 42 of the second end plate 32 and outer screw adapters 40 may be adapted to permit angulation of the removable hollow rod 14, for example, using a ball joint 90 with a rotatable ball 92 and socket 94, permitting the closed end 46 of the hollow rod 14 to be angled ($\theta$) within the fillable volume 18.

The one or more socket 94 of the ball joint 90 may extend through the second end plate 32 and be sealed against the inner surface 47 of the second end plate 32 by an inner O-ring 54 and outer washer 56 and supporting the rotatable ball 92 in a ball-and-socket joint configuration as known in the art. The rotatable ball 92 also extends through the second end plate 32 and further supports, for example, on a neck 95 of the ball 92, an inwardly extending screw adapter 96 (similar to the screw adapter 40) extending within the fillable volume 18 to receive the removable hollow rod 14 by a female thread fitting 98 permitting a screw connection between the female thread fitting 98 and the second attachment end 39. The rotatable ball can be rotated to angle (θ) the removable hollow rod 14 with respect to the axis of the socket 94.

A hollow channel 100 is formed through the rotatable ball 92 and the screw adapter 96 to allow radiation detectors and measurement devices 22 such as an active device 22 to pass from an exterior of the phantom capsule 12 through the hollow channel 100 and, finally, terminate within the connected removable hollow rod 14 which is suspended within the fillable volume 18. The radiation detectors and measurement devices 22 are described in further detail below.

Referring again to FIG. 1 and FIG. 2, the removable hollow rods 14 and/or the removable stoppers 50 may be attached to channels 42 of the first and second end plate 30, 32, or rotatable ball 92 of FIG. 6, in any combination as desired to allow the removable hollow rods 14 to support suspension of one or more phantom inserts 16 and, optionally, to allow radiation detectors and measurement devices 22 to be inserted within the removable hollow rods 14 to provide, e.g., a dosimetry measurement, as further described below.

It is understood that the present invention contemplates different configurations which allow any number of removable hollow rods 14, e.g., zero, one, two, three, four, five, six, seven, eight, nine, ten or more, to extend into or through the fillable volume 18 in a manner which permits phantom inserts 16 and/or radiation detectors and measurement devices 22 to be held within the fillable volume 18 as desired.

Referring specifically to FIG. 1, the phantom inserts 16 may include one or more phantom inserts 16 which may include solid anthropomorphic structures, e.g., a human heart, that are used for resolution and contrast assessments. The phantom inserts 16 may be made of tissue mimicking materials such as resins, gels, hydrogels, plastics, and a variety of 3D printed materials, and the like. The phantom inserts 16 may take various geometries and be homogenous or heterogenous in order to mimic tissue and tumors within the clinical target volume. The phantom inserts 16 may also be deformable and expand/contract, e.g., a fillable bladder. The phantom inserts 16 may further include radiation detectors and measurement devices 22 embedded into the phantom material to estimate radiation dose.

The anthropomorphic structures may be simulated tissues and organs that include the clinical target volume (CTV) for radiation and the surrounding organs at risk (OAR) which are healthy tissues and organs placed near the CTV. For example, during treatment of lung cancer, there is a desire to limit cardiac radiation exposure, which is linked to increased risk of cardiac disease and mortality, i.e., heart sparing radiotherapy techniques. In this respect, one or more phantom inserts 16 may be suspended within the phantom capsule 12 to simulate both the CTV and the surrounding OAR.

In one embodiment, anthropomorphic structures may be simulated as arrhythmogenic scar regions of the heart for noninvasive treatment with radiation therapy of ventricular tachycardia (VT).

The phantom inserts 16 may be suspended within the fillable volume 18 of the phantom capsule 12 (either freely suspended or held and supported by the hollow rods 14 or inserted into the hollow rods 14) to simulate various anatomical arrangements and configurations. The phantom inserts 16 may be constructed with preformed channels 62 corresponding to the diameter of the removable hollow rods 14 which allow the removable hollow rods 14 to extend therethrough and allowing the phantom inserts 16 to be suspended inside the phantom capsule 12.

Devices such as radiation detectors and measurement devices 22 such as dosimeters or scintillation (light) detectors or counters may be embedded within the phantom inserts 16, held within the hollow rods 14, or suspended within the fillable volume 18. The radiation detectors and measurement devices 22 may be passive or semi-passive devices 22a that do not provide direct readouts and can operate without any active means, e.g., radiolucent dosimeters such as thermoluminescent (TLD) or optically stimulated luminescence (OSL) chips or tags embedded within the phantom inserts 16 or suspended in the fluid 20 of the fillable volume 18.

The radiation detectors and measurement devices 22 may alternatively be active devices 22b that provide a direct reading of dose, e.g., electronic or digital dosimeters held within the hollow rods 14 and connected to an external display via connectors, e.g., electrical or fiber optic connectors, extending through the hollow rods 14 and out through the ends of the hollow rods 14 and circular hole 61 of the outer screw adapters 40 whereby a dose measurement may be displayed in a display device or monitor. The hollow rods 14 may be further filled with a water-based gel or fluid to reduce air-induced radiation beam disturbances surrounding radiation detectors and measurement devices 22 held within the hollow rods 14.

It is understood that any conventional passive or active radiation detectors and measurement devices 22 known in the art may be used within the phantom capsule 12.

Other medical devices that may be embedded within the phantom inserts 16, held within the hollow rods 14, or suspended within the fillable volume 18 include pacemaker leads, stents, wire meshes, etc. for clinical evaluation such as through image quality evaluation. Positions of the embedded medical devices may be controlled using distance measuring devices such as a caliper, ruler, or multiple known spacers, and the like. Referring still to FIG. 1, one or more radiation detectors and measurement devices 22 may be used within the phantom capsule 12 in order to detect the amount of radiation at a single or multiple "active" points 24 within and surrounding the phantom inserts 16. In one embodiment, at least one radiation detectors and measurement device 22, for example, one or two dosimeters, may be held within each of the hollow rods 14 extending inside the phantom inserts 16 to detect the amount of radiation within the CTV (high dose regions) or OAR (low dose regions) mimicked by the phantom inserts 16 and to facilitate the radiotherapy planning. It is understood that any number of conventional radiation detectors and measurement devices 22 may be used within the phantom capsule 12.

For imaging modalities that do not rely upon the mechanical properties of tissue, e.g., CT imaging, it may not be necessary to fill the phantom capsule 12 with a liquid or gel. Therefore, the fluid 20 within the fillable volume 18 may be air. However, for imaging modalities that rely upon mechanical properties of tissue, such as magnetization properties related to tissue relaxation, e.g., MRI, the fillable volume 18 of the phantom capsule 12 may be filled with a liquid or gel, such as deionized water or water based gel, following the placement of the phantom inserts 16 within the phantom capsule 12. The fluid 20 desirably provides comparable relaxation times to those of human tissue and may include water, agar, agarose and the like.

The fillable volume 18 may be filled with the fluid 20 through a one-way valve or check valve coupled to one or more of the channels 42 or one or more separate fill ports 76 (shown in FIG. 2) of the phantom capsule 12 allowing fluid 20 to substantially fill the fillable volume 18 prior to imaging. A syringe may be used to assist with filling the fillable volume 18 with the fluid 20. Once the fillable volume 18 is substantially filled, the fill port 76 is closed by a cap.

In certain embodiments, the one or more of the channels 42 or one or more separate fill ports 76 may assist with fluid flow through the fillable volume 18 while still sealing the phantom capsule 12. A hydraulic system including, e.g., a hydraulic pump creating a vacuum at a pump inlet and forcing liquid from a fluid source into an inlet line and to the pump and out the outlet line, may be used to assist with providing fluid flow through the fillable volume 18 to mimic fluid flow of the body.

In operation, the channels 42 of the first end plate 30 receives the removable hollow rods 14 and/or the removable stoppers 50 as desired to provide a desired configuration of hollow rods 14. As described above, the removable hollow rods 14 and/or the removable stoppers 50 may be screw tightened into the outer screw adapters 40 thus sealing the channels 42 from leakage.

Next, the phantom inserts 16 may be inserted into the phantom capsule 12 and may be supported by the removable hollow rods 14. The removable hollow rods 14 may be extended through the channels 62 of the phantom inserts 16 to be held in place.

In one exemplary embodiment, the phantom inserts 16 may model multiple tumors, e.g., three tumors, of the lungs whereby the lung tissue is represented by at least one phantom insert 16 supported by multiple removable hollow rods 14, e.g., three rods, with each tumor location marked by a removable hollow rods 14 extending through the phantom insert 16 at the tumor location and holding at least one radiation detectors and measurement devices 22 within each of the removable hollow rods 14 at the approximate location of the tumor. The channels 42 that are not connected to removable hollow rods 14 are filled with the removable stopper 50 thus water sealing the phantom capsule 12 from leakage.

Following the insertion of the phantom inserts 16, the second end plate 32 is attached to the cylindrical side wall 34, e.g., by fasteners 64, enclosing the phantom capsule 12. The radiation detectors and measurement devices 22 may be inserted into the hollow rods 14.

The fillable volume 18 may be filled with the fluid 20 thus permitting imaging such as MRI to be performed if desired. Fluid 20 may be omitted for other types of imaging modalities. Additional radiation detectors and measurement devices 22 may also be supported within the fluid 20 of the fillable volume 18.

During imaging, the motor drive assembly 82 may provide motion to the phantom capsule thus mimicking respiratory motion of, e.g., the diaphragm and lungs. The radiation detectors and measurement devices 22 may measure the amount of radiation dose that would be received under certain radiotherapy conditions at the tumor sites and at locations around the tumor sites, i.e., active points 24, to assist with radiotherapy treatment planning, image quality evaluation, target localization, and dosimetry measurements.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" can be understood to include one or more microprocessors that can communicate in a stand-alone and/or a distributed environment(s), and can thus be configured to communicate via wired or wireless communications with other processors, where such one or more processors can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A phantom assembly for medical imaging comprising:
   a watertight chamber having an outer wall supporting a volume therein and enclosed by first and second end plates; and
   at least one tube connector of the first and second end plates configured to removably receive at least one tube supported by the first and second end plates, each tube providing a volume therein.

2. The assembly of claim 1 further comprising at least one tube received by the at least one tube connector.

3. The assembly of claim 2 wherein the at least one tube connector comprises a channel receiving an end of the at least one tube.

4. The assembly of claim 2 further comprising at least one channel stopper insertable into the at least one channel if the at least one tube is not attached to the at least one channel.

5. The assembly of claim 4 wherein the at least one tube connector further comprises at least one screw adapter removably receiving the at least one tube or the at least one channel stopper on an exterior of the watertight chamber insert.

6. The assembly of claim 4 wherein the at least one channel stopper is comprise of threaded screw ends permitting the at least one channel stopper to be screw tightened into the at least one channel.

7. The assembly of claim 6 further comprising a gasket positioned between the first and second end plates and the at least one channel stopper.

8. The assembly of claim 4 wherein the at least one tube comprises threaded screw ends permitting the at least one tube to be screw tightened into the at least one channel.

9. The assembly of claim 8 further comprising a gasket positioned between the first and second end plates and the threaded screw ends of the at least one of tube.

10. The assembly of claim 1 further comprising a motor assembly connectable to the chamber and actuating movement of the chamber.

11. The assembly of claim 10 wherein the motor assembly is configured to move the chamber in a linear direction and non-linear directions.

12. The assembly of claim 1 further comprising at least one tube and a solid phantom supported by the at least one tube and mimicking at least part of a human body part.

13. The assembly of claim 1 further comprising at least one tube and at least one of a radiation measurement device, a radioactive material, a pacemaker lead, a stent, and a wire mesh supported within the watertight chamber.

14. The assembly of claim 13 wherein the at least one of a radiation measurement device, a radioactive material, a pacemaker lead, a stent, and wire mesh is held within the at least one tube.

15. The assembly of claim 1 wherein the watertight chamber is fillable with a fluid being a liquid or a gel.

16. The assembly of claim 15 further comprising a pump moving the fluid through the watertight chamber.

17. A method of imaging a phantom assembly comprising:
providing a watertight chamber having an outer wall supporting a volume therein and enclosed by first and second end plates and at least one tube removably supported by the first and second end plates, each tube providing a volume therein, wherein the first and second end plates each provide a plurality of channels of the first and second end plates and removably receiving the at least one tube;
connecting at least one tube to the plurality of channels;
connecting at least one stopper to channels where the at least one tube is not connected;
inserting a solid phantom mimicking at least part of a human body part into the watertight chamber and supported by the at least one tube;
sealing the watertight chamber; and
imaging the watertight chamber using a medical imaging technique.

18. The method of claim 17 further comprising inserting a radiation measurement device into the at least one tube prior to imaging and measuring a radiation dose.

19. The method of claim 17 further comprising filling the watertight chamber with a liquid prior to imaging.

20. The method of claim 17 wherein the medical imaging technique is any one of the following techniques: single photon emission computed tomography (SPECT), positron emission tomography (PET), computed tomography (CT), and magnetic resonance imaging (MRI).

* * * * *